United States Patent [19]

Hechenbleikner et al.

[11] 4,151,211
[45] Apr. 24, 1979

[54] BIS-(PHENOLIC)DIACETALS

[75] Inventors: Ingenuin Hechenbleikner, West Cornwall; William P. Enlow, Falls Village, both of Conn.

[73] Assignee: Borg-Warner Corporation, Chicago, Ill.

[21] Appl. No.: 883,753

[22] Filed: Mar. 6, 1978

[51] Int. Cl.$^2$ .................. C07C 43/30; C07C 149/36
[52] U.S. Cl. .................. 260/609 F; 260/45.85 S; 260/45.8 A; 260/45.95 C; 260/45.95 R; 260/340.6; 260/340.7; 260/340.9 R; 560/15; 568/592
[58] Field of Search .................. 260/45.85 S, 45.95 C, 260/45.95 H, 45.8 A, 340.6, 340.7, 340.9, 609 F, 45.95 R, 611 A; 560/15

[56] References Cited

U.S. PATENT DOCUMENTS

| | | | |
|---|---|---|---|
| 2,625,534 | 1/1953 | Thompson | 260/609 F |
| 2,831,030 | 5/1958 | Chenicek | 260/45.95 C |
| 2,838,571 | 6/1958 | Filbey | 260/45.95 H |
| 3,260,758 | 7/1966 | O'Shea | 260/609 F |
| 3,346,648 | 10/1967 | Worrel | 260/611 A |
| 3,948,946 | 4/1976 | Hofer et al. | 260/340.7 |
| 4,013,619 | 3/1977 | Schmidt | 260/340.7 |

FOREIGN PATENT DOCUMENTS 2501285 7/1975 Fed. Rep. of Germany.
448197 10/1975 U.S.S.R.

*Primary Examiner*—V. P. Hoke
*Attorney, Agent, or Firm*—Joseph Shekleton

[57] ABSTRACT

Phenolic acetals wherein the phenolic groups are hindered by ortho substituents. The acetals are prepared by the reaction of certain phenolic aldehydes with alcohols or mercaptans and are effective to impart thermal stability to olefin polymers.

4 Claims, No Drawings

BIS-(PHENOLIC)DIACETALS

BACKGROUND OF THE INVENTION

This invention relates to novel compounds which are effective to improve the heat stability of olefin polymers. It relates more particularly to olefin polymer compositions which contain such novel compounds.

Generally, polymer compositions are vulnerable to deterioration of physical and chemical properties during manufacture, storage, processing and use. To overcome such deterioration, or at least to inhibit it, there have been developed additive systems for the purpose of stabilizing polymeric materials with respect to physical and chemical degradation caused by exposure to environmental conditions. All of these additive systems, however, while effective for their intended purpose, are characterized by one or more shortcomings.

Olefin polymer compositions are especially vulnerable to oxidative degradation. The relatively high temperatures required for their customary processing procedures, such as roll milling, injection molding, extrusion and the like, invariably promote oxidation because these processes are carried out under ordinary atmospheric conditions, i.e., they are exposed to the oxygen of the atmosphere.

The significance of polymer oxidation lies in the adverse effect it has on polymer rheology, morphology, color, clarity, glass and other physical properties. Impact strength may be lost; the surface may become crazed or cracked. Even a darkening of the color may provide a sufficient aesthetic disadvantage as to render the polymer material unsuitable for its intended use.

SUMMARY OF THE INVENTION

The invention of this application is a phenolic acetal having the structural formula:

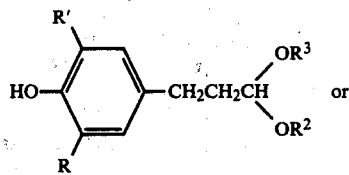

or

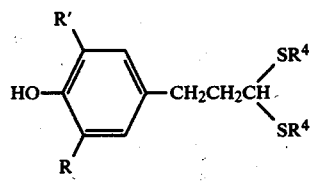

wherein R and R' are lower alkyl radicals, $R^2$ and $R^3$ are organic radicals, and $R^4$ is alkyl or $(CH_2)_n COOR^5$, where n is 1 or 2.

The term "lower alkyl" designates alkyl radicals of 3–8 carbon atoms. The lower alkyl radicals above preferably are tertiary, such as, for example, tertiary butyl, 2,2-dimethylpropyl, 2,2-dimethylbutyl, 2,2-dimethylamyl and 2,2,3-trimethylbutyl. Secondary and primary alkyl radicals are also contemplated, such as n-butyl, sec-amyl, n-hexyl and 2,3,3-trimethylbutane.

$R^2$ and $R^3$ are, as indicated, organic radicals. They may be two separate radicals or they may be combined as one radical, i.e., derived from a glycol. For example, they may be the same ethylene radical, or trimethylene, or propylene, etc. Preferred radicals include alkyl, alkylene, substituted alkylene, and aralkyl radicals.

$R^4$ and $R^5$ are alkyl radicals, including principally those containing 6–18 carbon atoms, e.g., octyl, isooctyl, decyl, dodecyl, tetradecyl, octadecyl, etc.

Alkylene radicals include ethylene, trimethylene, 2,2-dimethyltrimethylene, propylene, butylene and 1,4-butylene.

Substituted alkylene radicals include the residues from glycol, pentaerythritol, sorbitol, etc. It will be understood that the "residues" above may be hydroxy-substituted alkylenes or they may, depending on the relative proportions of reactants used in preparing the phenolic acetals herein, be low molecular weight polymers or bis-(phenolic)diacetals. Thus, the reaction of a 3(3,5-dialkyl-4-hydroxyphenyl)propionaldehyde with half a mol of pentaerythritol will produce a symmetrical diacetal, i.e., corresponding to the above structural formula A wherein $R^2$ and $R^3$ are a substituted alkylene radical. Other substituted alkylene radicals include the residues from glycols containing one or more substituents in their molecular structure, e.g., 2-chlorotrimethylene glycol, 2-methoxybutylene glycol-1,4 and 2-chloro-2-methoxytrimethylene glycol. A particularly preferred substituted alkylene radical is that having the structure:

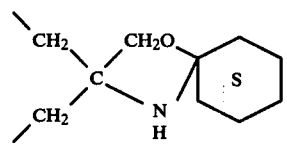

Aralkyl radicals contemplated herein include benzyl, phenylethyl, phenylpropyl and such radicals wherein the benzene rings thereof contain hydroxyl and lower alkyl substituents. Illustrative examples include 4-hydroxybenzyl, 2(3,5-di-n-butylphenyl)ethyl, 2(3,5-ditertiarybutyl-4-hydroxyphenyl)ethyl, 3(3,5-ditertiarybutyl-4-hydroxyphenyl)propyl. The lower alkyl substituents contain 3–8 carbon atoms and may be substituted on the ortho, meta or para positions; there may be 1–3 of such substituents per benzene ring. The hydroxyl group likewise may be on the ortho, meta or para positions although it is preferred that it be on the para position. A preferred aralkyl radical, i.e., $R^2$ and $R^3$, is one having the structure:

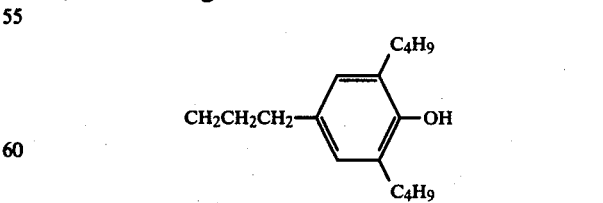

where $C_4H_9$ is a tertiarybutyl substituent.

The $R^4$ radicals preferably are those alkyl radicals containing 6–18 carbon atoms. Dodecyl is preferred.

A particularly preferred phenolic acetal is a bis-(phenolic)diacetal having the structural formula:

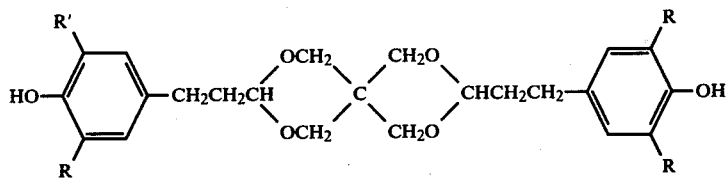

wherein R and R' are lower alkyl radicals. It will be noted that the above compounds contain 3,5-dialkyl-4-hydroxyphenyl groups bound to a pentaerythritol nucleus through a CH2CH2CH group.

The phenolic acetals are notably effective to impart thermal stability to olefin polymers. That is, an olefin polymer composition containing a small proportion of such an acetal will be resistant to deterioration ordinarily resulting from exposure to elevated temperatures.

The phenolic acetals herein may be prepared by reaction of an alcohol (including glycols) or mercaptan with a 3-(3,5-dialkyl-4-hydroxyphenyl)propionaldehyde, as illustrated by the following equation:

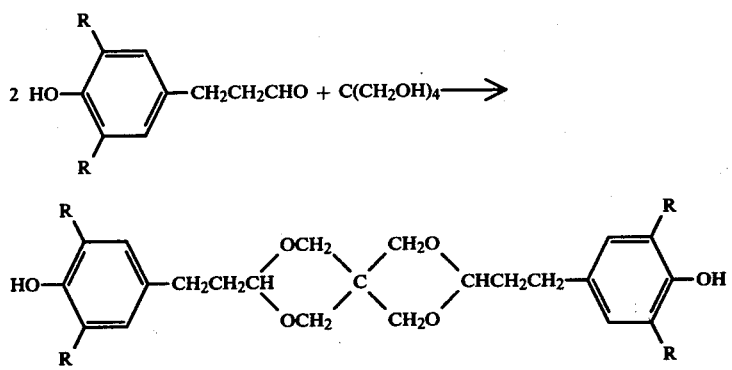

The reaction is catalyzed by acidic materials such as mineral acids, acidic salts, etc. p-Toluenesulfonic acid, for example, is a convenient and satisfactory catalyst. Approximately stoichiometric proportions of reactants are used, i.e., two mols of phenolic aldehyde per mol of pentaerythritol. Where the alcohol reactant is a monohydric alcohol or mercaptan, the stoichiometry will, of course, be different and will require reaction of two mols of alcohol (or mercaptan) with one mol of the phenolic aldehyde. Typically, the reactants plus catalyst are heated with stirring for a brief period and the product mixture purified as desired by washing with a solvent or crystallization from a solvent such as heptane. A solvent may be employed in the reaction but is not necessary.

The following examples, which are merely illustrative and in no way limiting, show such a preparation.

EXAMPLE 1

A mixture of 5.34 parts (0.02 mol) of 3(3,5-ditertiarybutyl-4-hydroxyphenyl)propionaldehyde, 1.36 parts (0.01 mol) of pentaerythritol, 10 parts of water and 0.1 g. of p-toluenesulfonic acid is heated with stirring at 150° C./10 mm. for 15 minutes, then to a final temperature of 150° C./0.5 mm. The cooled residue is extracted with benzene and the benzene extract found, by means of infrared analyses, to be free of hydroxyl groups and to contain only a trace of carbonyl groups. The benzene is evaporated away from a residue which is crystallized from heptane, yielding 3.5 g. of solid, M.P., 168°–170° C.

EXAMPLE 2

A mixture of 13.1 parts (0.05 mol) of 3(3,5-ditertiarybutyl-4-hydroxyphenyl)propionaldehyde, 20.2 parts (0.1 mol) of dodecyl mercaptan, 85 parts of toluene and 0.1 part of p-toluenesulfonic acid is heated at reflux temperature for two hours and then stripped to a substantially water-free residue. The residue is a viscous, yellow liquid weighing 32 g. Infrared analysis shows the absence of carbonyl and mercapto groups.

EXAMPLE 3

A mixture of 52 parts (0.20 mol) of 3(3,5-ditertiarybutyl-4-hydroxyphenyl)propionaldehyde, 110 parts (0.41 mol) of 3(3,5-ditertiarybutyl-4-hydroxyphenyl)propyl alcohol, 50 parts of a molecular sieve (Linde, 5A) and 430 parts of toluene is stirred at room temperature while dry hydrogen chloride is bubbled in for 15 minutes (pH: 3). Stirring is continued at room temperature for 90 hours, additional dry hydrogen chloride being bubbled in after 16 hours to restore the pH from 5 to 3. The molecular sieve is removed by filtration and the filtrate evaporated to a viscous, liquid residue weighing 15.5 g. Infrared analyses show only a trace of hydroxyl groups and no carbonyl groups.

The efficacy of the phenolic acetals herein is shown by the data in Table I. That data is obtained from a heat stability test wherein plaques of 25-mil thickness are rotated in an oven at 150° C. until the appearance of surface crazing, at which point they are deemed to have failed. The plaques are injection molded from material that has been extruded into pellets. Each of the test plaques consists essentially of the following:

100 parts polypropylene
0.10 part calcium stearate plus indicated amounts of the phenolic diacetal and distearyl dithiopropionate (DSTDP). Each reported test result is an average of three actual test results.

TABLE I

| Phenolic Acetal | Amount | DSTDP* | Rating (hours to failure) |
|---|---|---|---|
| Product of Example 1 | | | |
| Test 1 | 0 | .45 | 300 |
| | .1 | .35 | 836 |

TABLE I-continued

| Phenolic Acetal | Amount | DSTDP* | Rating (hours to failure) |
|---|---|---|---|
| | .2 | .25 | 972 |
| | .35 | .1 | 820 |
| | .45 | 0 | 636 |
| Test 2 | 0 | .25 | 133 |
| | .1 | .25 | 883 |
| Product of Example 2 | | | |
| | 0 | .25 | 309 |
| | 0 | .45 | 432 |
| | .1 | .35 | 717 |
| | .2 | .25 | 812 |
| | .35 | .1 | 812 |
| | .45 | 0 | 788 |
| Product of Example 3 | | | |
| | 0 | .2 | 120 |
| | 0 | .3 | 168 |
| | .2 | .25 | 305 |

*Distearylthiodipropionate

The data in Table II is obtained from a color aging test. Three of the above 25-mil plaques are placed in an oven at 150° C. and then are removed, one at a time, at 200, 400 and 600 hours. The color of each and of an unheated plaque are noted, on a scale of 0 (black) to 100 (white).

TABLE II

| | Hours | | | |
|---|---|---|---|---|
| Phenolic Acetal | 0 | 100 | 200 | 300 |
| Product of Example 1 | 82 | 79 | 79 | 77 |
| Product of Example 2 | 82 | 78 | 77 | 77 |

It will be noted that each of the above test samples lost virtually none of its color even on heating at 150° C. for 300 hours.

The olefin polymer may be either a homopolymer or copolymer, but, if the latter, it should comprise at least about 90% of olefin units. Polymers contemplated include polyethylene (low density and high density), polypropylene, polyisobutylene, EPDM polymers, copolymers of ethylene and propylene, copolymers of ethylene and vinyl acetate, copolymers of propylene and vinyl acetate, copolymers of ethylene or propylene with up to 10% of a higher ($C_4$–$C_6$) monoolefin, and terpolymers of ethylene and propylene. Polymers of ethylene and propylene are preferred and polypropylene is especially preferred.

The concentration of phenolic acetal which is to be used in the above olefin polymer compositions should be within from about 0.01 to about 1.0 parts per 100 parts of resin (PHR), i.e., olefin polymer.

It usually is desirable to use a dialkyl thiodipropionate in combination with the phenolic acetal to achieve maximum and more efficient heat stabilization. The alkyl groups in such dialkyl thiodipropionate are those having 8-20 carbon atoms and distearyl thiodipropionate is preferred. From about 0.05 to about 1.0 PHR.

All parts and percentages herein, unless otherwise expressly stated, are by weight.

We claim:

1. A phenolic acetal having the structural formula:

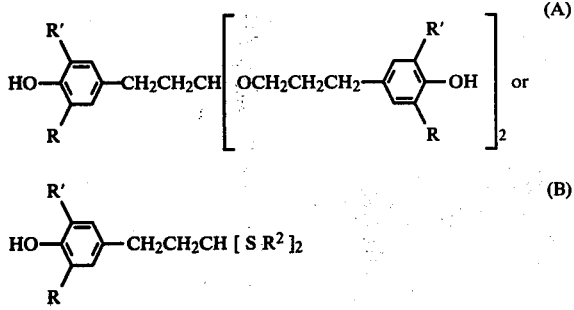

wherein R and R' are lower alkyl groups and $R^2$ is an alkyl of 6–18 carbon atoms.

2. The phenolic acetal of claim 1 wherein R and R' are tertiary alkyl groups.

3. The phenolic acetal of claim 1 wherein R and R' are tertiary butyl groups.

4. The phenolic acetal of claim 1 having the structural formula (B) wherein $R^2$ is dodecyl.

* * * * *